(12) United States Patent
Nomura et al.

(10) Patent No.: US 7,521,430 B2
(45) Date of Patent: Apr. 21, 2009

(54) N-GLUCOSIDE COMPOUNDS HAVING AN INHIBITORY ACTIVITY AGAINST SODIUM-DEPENDENT GLUCOSE TRANSPORTER

(75) Inventors: Sumihiro Nomura, Osaka (JP); Toshiaki Sakamoto, Osaka (JP); Kiichiro Ueta, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 246 days.

(21) Appl. No.: 10/566,585

(22) PCT Filed: Jul. 30, 2004

(86) PCT No.: PCT/JP2004/011311

§ 371 (c)(1), (2), (4) Date: Jul. 28, 2006

(87) PCT Pub. No.: WO2005/012321

PCT Pub. Date: Feb. 10, 2005

(65) Prior Publication Data

US 2007/0060545 A1     Mar. 15, 2007

Related U.S. Application Data

(60) Provisional application No. 60/491,523, filed on Aug. 1, 2003.

(51) Int. Cl.
*A01N 43/04* (2006.01)
*A61K 31/70* (2006.01)
*C07H 5/06* (2006.01)
*C07H 19/00* (2006.01)

(52) U.S. Cl. .................. 514/42; 536/18.7; 536/22.1; 536/29.1

(58) Field of Classification Search .................. None
See application file for complete search history.

(56) References Cited

U.S. PATENT DOCUMENTS

| 7,419,959 B2 * | 9/2008 | Eckhardt et al. ............... 514/23 |
| 2004/0053855 A1 | 3/2004 | Fujikura et al. |
| 2004/0063646 A1 | 4/2004 | Fujikura et al. |

FOREIGN PATENT DOCUMENTS

| EP | 1 270 584 A1 | 1/2003 |
| WO | WO-01/27128 A1 | 4/2001 |
| WO | WO-01/74834 A1 | 10/2001 |
| WO | WO-03/020737 A1 | 3/2003 |

OTHER PUBLICATIONS

Wolff, Manfred E. "Burger's Medicinal Chemistry, 5ed, Part I", John Wiley & Sons, 1995, pp. 975-977.*
Goodman & Gilman's: The Pharmacological Basis of Therapeutics, 10th Edition, McGraw-Hill Medical Publishing Division, 2001, pp. 54-56.*
Banker, G.S. et al., "Modern Pharmaceuticals, 3rd Ed.", Marcel Dekker, New York, 1996, p. 596.*
Manis M O et al., Drug Metabolism and Disposition, Williams and Wilkins., vol. 14, No. 2, 1986, pp. 166-174.
P. Lin et al., Synthesis, 2003, pp. 255-261.

* cited by examiner

*Primary Examiner*—Traviss C McIntosh, III
(74) *Attorney, Agent, or Firm*—Birch, Stewart, Kolasch & Birch, LLP

(57) ABSTRACT

A compound of the formula:

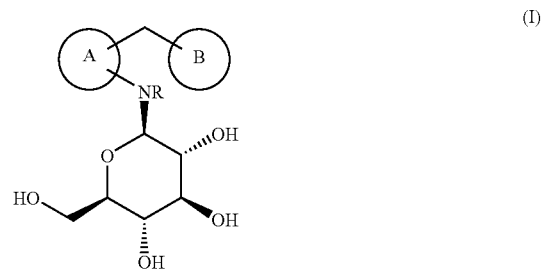

(I)

wherein Ring A and Ring B are (1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring, (2) Ring A is an optionally substituted benzene ring, and Ring B is an optionally substituted unsaturated monocyclic heterocyclic ring, an optionally substituted unsaturated fused heterobicyclic ring, or an optionally substituted benzene ring, or (3) Ring A is an optionally substituted unsaturated fused heterobicyclic ring, wherein —NR— group and —CH$_2$— group are both on the same ring of the unsaturated fused heterobicyclic ring, and Ring B is an optionally substituted monocyclic unsaturated heterocyclic ring, an optionally substituted unsaturated fused heterobicyclic ring, or an optionally substituted benzene ring; and R is a hydrogen atom, a lower alkyl group, a lower alkanoyl group or a lower alkoxycarbonyl group, or a pharmaceutically acceptable salt thereof, or a prodrug thereof.

7 Claims, No Drawings

N-GLUCOSIDE COMPOUNDS HAVING AN INHIBITORY ACTIVITY AGAINST SODIUM-DEPENDENT GLUCOSE TRANSPORTER

This application is the National Phase of PCT International application No. PCT/JP2004/01131 filed on Jul. 30, 2004 which claims priority under 35 U.S.C. 119(e) on U.S. Provisional Application No. 60/491,523 filed on Aug. 1, 2003, the entire contents of which are hereby incorporated by reference.

TECHNICAL FIELD

The present invention relates to a novel compound having an inhibitory activity against sodium-dependent glucose transporter (SGLT) being present in the intestine or kidney.

BACKGROUND ART

Although diet therapy and exercise therapy are essential in the treatment of diabetes mellitus, when these therapies do not sufficiently control the conditions of patients, insulin or an oral antidiabetic agent is additionally used. At the present, there have been used as an antidiabetic agent biguanide compounds, sulfonylurea compounds, insulin resistance improving agents and α-glucosidase inhibitors. However, these antidiabetic agents have various side effects. For example, biguanide compounds cause lactic acidosis, sulfonylurea compounds cause significant hypoglycemia, insulin resistance improving agents cause edema and heart failure, and α-glucosidase inhibitors cause abdominal bloating and diarrhea. Under such circumstances, it has been desired to develop novel drugs for treatment of diabetes mellitus having no such side effects.

Recently, it has been reported that hyperglycemia participates in the onset and progressive impairment of diabetes mellitus, i.e., glucose toxicity theory. That is, chronic hyperglycemia leads to decrease insulin secretion and further to decrease insulin sensitivity, and as a result, the blood glucose concentration is increased so that diabetes mellitus is self-exacerbated [cf., Diabetologia, vol. 28, p. 119 (1985); Diabetes Care, vol. 13, p. 610 (1990), etc.]. Therefore, by treating hyperglycemia, the aforementioned self-exacerbating cycle is interrupted so that the prophylaxis or treatment of diabetes mellitus is made possible.

As one of the methods for treating hyperglycemia, it is considered to excrete an excess amount of glucose directly into urine so that the blood glucose concentration is normalized. For example, by inhibiting sodium-dependent glucose transporter being present at the proximal convoluted tubule of kidney, the re-absorption of glucose at the kidney is inhibited, by which the excretion of glucose into urine is promoted so that the blood glucose level is decreased. In fact, it is confirmed that by continuous subcutaneous administration of phlorizin having SGLT inhibitory activity to diabetic animal models, hyperglycemia is normalized and the blood glucose level thereof can be kept normal for a long time so that the insulin secretion and insulin resistance are improved [cf., Journal of Clinical Investigation, vol. 79, p. 1510 (1987); ibid., vol. 80, p. 1037 (1987); ibid., vol. 87, p. 561 (1991), etc.].

In addition, by treating diabetic animal models with SGLT inhibitory agents for a long time, insulin secretion response and insulin sensitivity of the animals are improved without incurring any adverse affects on the kidney or imbalance in blood levels of electrolytes, and as a result, the onset and progress of diabetic nephropathy and diabetic neuropathy are prevented [cf., Journal of Medicinal Chemistry, vol. 42, p. 5311 (1999); British Journal of Pharmacology, vol. 132, p. 578 (2001), etc.].

From the above, SGLT inhibitors may be expected to improve insulin secretion and insulin resistance by decreasing the blood glucose level in diabetic patients and further prevent the onset and progress of diabetes mellitus and diabetic complications.

WO 01/27128 discloses an aryl C-glycoside compound having the following structure.

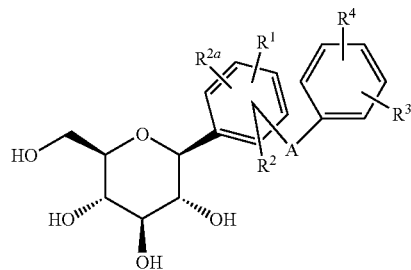

WO 01/68660 disclosed an aryl O-glycoside compound having the following structure.

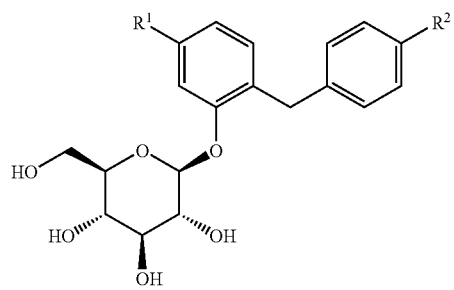

WO 01/74834 discloses an aryl O-glycoside compound of the following formula.

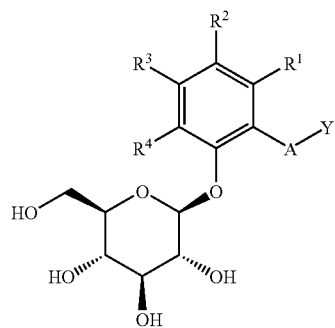

wherein Y is a group of the formula:

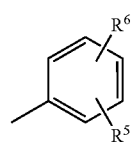

or a heteroaryl group.

WO 02/53573 discloses an O-pyrazole glucoside compound of the following formula.

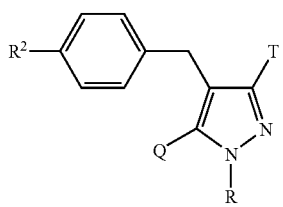

wherein T or Q is the formula:

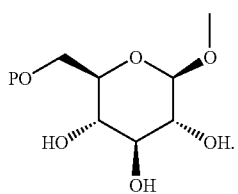

WO 03/020737 discloses an O-pyrazole glucoside compound of the following formula.

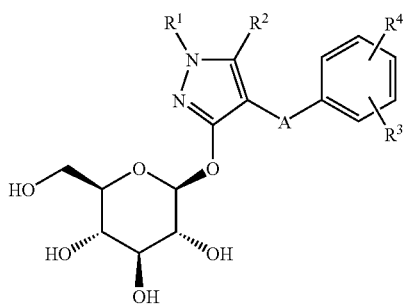

These compounds are disclosed to be useful as an SGLT inhibitor in the prophylaxis or treatment of diabetes mellitus, etc.

DISCLOSURE OF INVENTION

The present invention relates to an N-glucoside compound of the following formula I, or a pharmaceutically acceptable salt thereof, or a prodrug thereof.

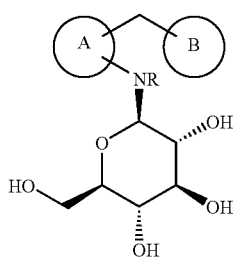

(I)

wherein Ring A and Ring B are (1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring, (2) Ring A is an optionally substituted benzene ring, and Ring B is an optionally substituted unsaturated monocyclic heterocyclic ring, an optionally substituted unsaturated fused heterobicyclic ring, or an optionally substituted benzene ring, or (3) Ring A is an optionally substituted unsaturated fused heterobicyclic ring, wherein —NR— group and —CH$_2$— group are both on the same ring of the unsaturated fused heterobicyclic ring, and Ring B is an optionally substituted monocyclic unsaturated heterocyclic ring, an optionally substituted unsaturated fused heterobicyclic ring, or an optionally substituted benzene ring; and R is a hydrogen atom, a lower alkyl group, a lower alkanoyl group or a lower alkoxycarbonyl group.

The compound of the formula I exhibits an inhibitory activity against sodium-dependent glucose transporter being present in the intestine and the kidney of mammalian species, and is useful in the treatment of diabetes mellitus or diabetic complications such as diabetic retinopathy, diabetic neuropathy, diabetic nephropathy, delayed wound healing.

BEST MODE FOR CARRYING OUT THE INVENTION

Hereinafter, the present compound (I) is illustrated in more detail.

The definitions for each term used in the description of the present invention are listed below.

The "halogen atom" or the "halo" means chlorine, bromine, fluorine and iodine, and chlorine and fluorine are preferable.

The "alkyl group" means a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof. Further, the alkyl group may optionally be substituted by 1 to 4 substituents as listed below, if necessary.

The "alkylene group" or the "alkylene" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc. If necessary, the alkylene group may optionally be substituted in the same manner as the above-mentioned "alkyl group".

Where alkylene groups as defined above attach at two different carbon atoms of the benzene ring, they form an annelated five, six or seven membered carbocycle together with the carbon atoms to which they are attached, and may optionally be substituted by one or more substituents defined below.

The "alkenyl group" means a straight or branched monovalent hydrocarbon chain having 2 to 12 carbon atoms and having at least one double bond. Preferable alkenyl group is a straight chain or branched chain alkenyl group having 2 to 6 carbon atoms, and the straight chain or branched chain alkenyl group having 2 to 4 carbon atoms is more preferable. 3-pentenyl group, 2-hexenyl group, 3-hexenyl group, 2-heptenyl group, 3-heptenyl group, 4-heptenyl group, 3-octenyl group, 3-nonenyl group, 4-decenyl group, 3-undecenyl group, 4-dodecenyl group, 4,8,12-tetradecatrienyl group, etc. The alkenyl group may optionally be substituted by 1 to 4 substituents as mentioned below, if necessary.

The "alkenylene group" means a straight or branched divalent hydrocarbon chain having 2 to 12 carbon atoms and having at least one double bond. The straight chain or branched chain alkenylene group having 2 to 6 carbon atoms is preferable, and the straight chain or branched chain alkenylene group having 2 to 4 carbon atoms is more preferable. Examples thereof are vinylene group, propenylene group, butadienylene group, etc. If necessary, the alkylene group may optionally be substituted by 1 to 4 substituents as mentioned below, if necessary.

Where alkenylene groups as defined above attach at two different carbon atoms of the benzene ring, they form an annelated five, six or seven membered carbocycle (e.g., a fused benzene ring) together with the carbon atoms to which they are attached, and may optionally be substituted by one or more substituents defined below.

The "alkynyl group" means a straight or branched monovalent hydrocarbon chain having at least one triple bond. The preferable alkynyl group is a straight chain or branched chain alkynyl group having 2 to 6 carbon atoms, and the straight chain or branched chain alkynyl group having 2 to 4 carbon atoms is more preferable. Examples thereof are 2-propynyl group, 3-butynyl group, 2-butynyl group, 4-pentynyl group, 3-pentynyl group, 2-hexynyl group, 3-hexynyl group, 2-heptynyl group, 3-heptynyl group, 4-heptynyl group, 3-octynyl group, 3-nonynyl group, 4-decynyl group, 3-undecynyl group, 4-dodecynyl group, etc. The alkynyl group may optionally be substituted by 1 to 4 substituents as mentioned below, if necessary.

The "cycloalkyl group" means a monocyclic or bicyclic monovalent saturated hydrocarbon ring having 3 to 12 carbon atoms, and the monocyclic saturated hydrocarbon group having 3 to 7 carbon atoms is more preferable. Examples thereof are a monocyclic alkyl group and a bicyclic alkyl group such as cyclopropyl group, cyclobutyl group, cyclopentyl group, cyclohexyl group, cycloheptyl group, cyclooctyl group, cyclodecyl group, etc. These groups may optionally be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary).

The "cycloalkylidene group" means a monocyclic or bicyclic divalent saturated hydrocarbon ring having 3 to 12 carbon atoms, and the monocyclic saturated hydrocarbon group having 3 to 6 carbon atoms is preferable. Examples thereof are a monocyclic alkylidene group and a bicyclic alkylidene group such as cyclopropylidene group, cyclobutylidene group, cyclopentylidine group, cyclohexylidene group, etc. These groups may optionally be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary).

The "cycloalkenyl group" means a monocyclic or bicyclic monovalent unsaturated hydrocarbon ring having 4 to 12 carbon atoms and having at least one double bond. The preferable cycloalkenyl group is a monocyclic unsaturated hydrocarbon group having 4 to 7 carbon atoms. Examples thereof are monocyclic alkenyl groups such as cyclopentenyl group, cyclopentadienyl group, cyclohexenyl group, etc. These groups may optionally be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary).

The "cycloalkynyl group" means a monocyclic or bicyclic unsaturated hydrocarbon ring having 6 to 12 carbon atoms, and having at least one triple bond. The preferable cycloalkynyl group is a monocyclic unsaturated hydrocarbon group having 6 to 8 carbon atoms. Examples thereof are monocyclic alkynyl groups such as cyclooctynyl group, cyclodecynyl group. These groups may optionally be substituted by 1 to 4 substituents as mentioned below, if necessary. Besides, the cycloalkynyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary).

The "aryl group" means a monocyclic or bicyclic monovalent aromatic hydrocarbon group having 6 to 10 carbon atoms. Examples thereof are phenyl group, naphthyl group (including 1-naphthyl group and 2-naphthyl group). These groups may optionally be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally have an oxygen atom, a nitrogen atom, a sulfur atom, SO or $SO_2$ within the ring, if necessary).

The "unsaturated monocyclic heterocyclic ring" means an unsaturated monocyclic hydrocarbon ring containing 1-4 heteroatoms independently selected from a nitrogen atom, an oxygen atom and a sulfur atom, and the preferable one is a 4- to 7-membered unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, tetrazole, etc. Among them, pyridine, pyrimidine, pyrazine, furan, thiophene, pyrrole, imidazole, oxazole, and thiazole can be preferably used. The "unsaturated monocyclic heterocyclic ring" includes possible N— or S-oxides thereof. Furthermore, the "unsaturated monocyclic heterocyclic ring" may optionally be substituted by 1-4 substituents as mentioned below, if necessary.

The "unsaturated fused heterobicyclic ring" means a saturated or unsaturated hydrocarbon ring condensed with the "unsaturated monocyclic heterocyclic ring", where said saturated hydrocarbon ring and said unsaturated hydrocarbon ring may optionally contain an oxygen atom, a nitrogen atom, or a sulfur atom within the ring, if necessary. The "unsaturated fused heterobicyclic ring" includes, for example, benzothiophene, indole, etc., and also includes possible N— or S-oxides thereof. Furthermore, the "unsaturated fused heterobicyclic ring" includes the monocyclic unsaturated heterocyclic ring substituted by an alkylene group. The unsaturated fused heterobicyclic ring may optionally be substituted by 1-4 substituents as mentioned below, if necessary.

The "heterocyclyl" means a monovalent group of the above-mentioned monocyclic unsaturated heterocyclic ring or unsaturated fused heterobicyclic ring and a monovalent group of the saturated version of the above-mentioned monocyclic unsaturated heterocyclic ring or unsaturated fused heterobicyclic ring. If necessary, the heterocyclyl may optionally be substituted by 1 to 4 substituents as mentioned below.

The "alkanoyl group" means a formyl group and ones formed by binding an "alkyl group" to a carbonyl group.

The "alkoxy group" means ones formed by binding an "alkyl group" to an oxygen atom.

The substituent for the above each group includes, for example, a halogen atom (e.g., fluorine, chlorine, bromine, iodine), a nitro group, a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group. Each group as mentioned above may optionally be substituted by these substituents.

Further, the terms such as a haloalkyl group, a halo-lower alkyl group, a haloalkoxy group, a halo-lower alkoxy group, or a halophenyl group, or a haloheterocyclyl group means an alkyl group, a lower alkyl group, an alkoxy group a lower alkoxy group, a phenyl group, or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms. Similarly, the terms such as a hydroxyalkyl group, a hydroxy-lower alkyl group, a hydroxyalkoxy group, a hydroxy-lower alkoxy group mean an alkyl group, etc., being substituted by one or more hydroxy groups. Preferable ones are an alkyl group, etc., being substituted by 1 to 4 hydroxy groups, and more preferable ones are an alkyl group, etc., being substituted by 1 to 2 hydroxy groups. Further, the terms such as an alkoxyalkyl group, a lower alkoxyalkyl group, an alkoxy-lower alkyl group, a lower alkoxy-lower alkyl group, an alkoxyalkoxy group, a lower alkoxyalkoxy group, an alkoxy-lower alkoxy group, a lower alkoxy-lower alkoxy group means an alkyl group, etc., being substituted by one or more alkoxy groups. Preferable ones are an alkyl group, etc., being substituted by 1 to 4 alkoxy groups, and more preferable ones are an alkyl group, etc., being substituted by 1 to 2 alkoxy groups.

The terms "arylakyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise.

The "prodrug" means an ester or carbonate, which is formed by reacting one or more hydroxy groups of the compound of the formula I with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the formula I with an α-amino acid or a β-amino acid, etc. using a condensing agent by a conventional method.

The pharmaceutically acceptable salt of the compound of the formula I includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl)aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, aceticacid, propionicacid, oxalicacid, malonicacid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compound of the present invention also includes a mixture of stereoisomers, or each pure or substantially pure isomer. For example, the present compound may optionally have one or more asymmetric center at a carbon atom containing any one of substituents. Therefore, the compound of the formula I may exist in the form of enantiomer or diastereomer, or a mixture thereof. When the present compound contains a double bond, the present compound may exist in the form of geometric isomerism (cis-compound, trans-compound), and when the present compound contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compounds. When the present compound is obtained in the form of a diastereomer or enantiomer, they can be separated by a conventional method such as chromatography or fractional crystallization.

In addition, the present compound (I) includes an intramolecular salt, hydrate, solvate or polymorphism thereof.

The optionally, substituted unsaturated monocyclic heterocyclic ring of the present invention includes an unsaturated monocyclic heterocyclic ring which may optionally be substituted by 1-5 substituents selected from the group consisting of a halogen atom, a nitro group, a cyano group, an oxo group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, a sulfamoyl group, s mono- or di-alkylsulfamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group wherein each substituent may optionally be further substituted by these substituents.

The optionally substituted unsaturated fused heterobicyclic ring of the present invention includes an unsaturated fused heterobicyclic ring which may optionally be substituted by 1-5 substituents selected from the group consisting of a halogen atom, a nitro group, a cyano group, an oxo group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, acycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, a sulfamoyl group, s mono- or di-alkylsulfamoyl group, an alkylsulfinyl group, an alkenylsulfinyl group, an alkynylsulfinyl group, a cycloalkyisulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group wherein each substituent may optionally be further substituted by these substituents.

The optionally substituted benzene ring of the present invention includes a benzene ring which may optionally be substituted by 1-5 substituents selected from the group consisting of a halogen atom, a nitro group, a cyano group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, a sulfamoyl group, s mono- or di-alkylsulfamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, a heterocyclylsulfonyl group, an alkylene group, an alkyleneoxy group, an alkylenedioxy group, and an alkenylene group, wherein each substituent may optionally be further substituted by these substituents. Moreover, the optionally substituted benzene ring includes a benzene ring substituted with an alkylene group to form an annelated carbocycle together with the carbon atoms to which they are attached, and also includes a benzene ring substituted with an alkenylene group to form an annelated carbocycle such as a fused benzene ring and a fused cyclopentadiene ring together with the carbon atoms to which they are attached.

The optionally substituted unsaturated monocyclic heterocyclic ring is preferably an unsaturated monocyclic heterocyclic ring which may optionally be substituted by 1-3 substituents selected from the group consisting of a halogen atom, a hydroxyl group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylthio group, an alkylsulfinyl group, an alkylsulfonyl group, an arylsulfonyl group, a sulfamoyl group, s mono- or di-alkylsulfaamoyl group, a heterocyclyl group, and an oxo group.

The optionally substituted unsaturated fused heterobicyclic ring is preferably an unsaturated fused heterobicyclic ring which may optionally be substituted by 1-3 substituents selected from the group consisting of a halogen atom, a hydroxyl group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylthio group, an alkylsulfinyl group, an alkylsulfonyl group, an arylsulfonyl group, a sulfamoyl group, s mono- or di-alkylsulfamoyl group, a heterocyclyl group, and an oxo group.

The optionally substituted benzene ring is preferably a benzene ring which may optionally be substituted by 1-3 substituents selected from the group consisting of a halogen atom, a hydroxyl group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylthio group, an alkylsulfinyl group, an alkylsulfonyl group, an arylsulfonyl group, a sulfamoyl group, s mono- or di-alkylsulfamoyl group, a heterocyclyl group, an alkylene group, an alkyleneoxy group, an alkylenedioxy group, and an alkenylene group.

In a preferred embodiment of the present invention, the optionally substituted unsaturated monocyclic heterocyclic ring is an unsaturated monocyclic heterocyclic ring which may optionally be substituted by 1-3 substituents selected from the group consisting of a halogen atom, a hydroxyl group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, a sulfamoyl group, s mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group;

the optionally substituted unsaturated fused heterobicyclic ring is an unsaturated fused heterobicyclic ring which may optionally be substituted by 1-3 substituents selected from the group consisting of a halogen atom, a hydroxyl group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, a sulfamoyl group, s mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group; and the optionally substituted benzene ring is a benzene ring which may optionally be substituted by 1-3 substituents selected from the group consisting of a halogen atom, a hydroxyl group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, a sulfamoyl group, s mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

wherein each of the above mentioned substituents on the unsaturated monocyclic heterocyclic ring, the unsaturated fused heterobicyclic ring and the benzene ring may further be substituted by 1-3 substituents, independently selected from the group consisting of a halogen atom, a hydroxyl group, a cyano group, an alkyl group, a haloalkyl group, an alkoxy group, a haloalkoxy group, an alkanoyl group, an alkylthio group, an alkylsulfonyl group, a mono- or di-alkylamino group, a carboxyl group, an alkoxycarbonyl group, a phenyl group, an alkyleneoxy group, an alkylenedioxy group, and an oxo group.

In a more preferred embodiment of the present invention, the optionally substituted unsaturated monocyclic heterocyclic ring is an unsaturated monocyclic heterocyclic ring which may optionally be substituted by 1-3 substituents selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, and an oxo group;

the optionally substituted unsaturated fused heterobicyclic ring is a unsaturated fused heterobicyclic ring which may optionally be substituted by 1-3 substituents selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, and an oxo group; and the optionally substituted benzene ring is a benzene ring which may optionally be substituted by 1-3 substituents selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, an alkylene group, and an alkenylene group;

wherein each of the above mentioned substituents on the unsaturated monocyclic heterocyclic ring, the unsaturated fused heterobicyclic ring and the benzene ring may further be substituted by 1-3 substituents, independently selected from the group consisting of a halogen atom, a cyano group, a hydroxy group, an alkyl group, a haloalkyl group, an alkoxy group, a haloalkoxy group, an alkanoyl group, a mono- or di-alkylamino group, a carboxyl group, a phenyl group, an alkylenedioxy group, an alkyleneoxy group, and an alkoxycarbonyl group.

In another more preferred embodiment of the present invention, Ring A is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, an alkylene group, and an alkenylene group, and Ring B is a benzene ring, which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, an alkylene group, and an alkenylene group; wherein the substituent on Ring A and Ring B may optionally be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, and an alkoxycarbonyl group.

In a further more preferred embodiment of the present invention, Ring A is an unsaturated monocyclic heterocyclic ring which may optionally be substituted by a substituent selected from the group consisting of a halogen atom, a lower alkyl group, a halo-lower alkyl group, a lower alkoxy group, and an oxo group, or Ring A is a benzene ring which may optionally be substituted by a substituent selected from the group consisting of a halogen atom, a lower alkyl group, a halo-lower alkyl group, a lower alkoxy group, and a phenyl group;

Ring B is a benzene ring which may optionally be substituted by a substituent selected from the group consisting of a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; and a heterocyclyl group optionally substituted by a halogen atom, a cyano group, a lower alkyl group, a halo-lower alkyl group, a lower alkoxy group, or a mono- or di-lower alkylamino group; or an unsaturated monocyclic heterocyclic ring which may optionally be substituted by a substituent selected from the group consisting of a halogen atom; a cyano group; a lower alkyl group; a halo-lower alkyl group; a phenyl-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; and a heterocyclyl group optionally substituted by a halogen atom, a cyano group, a lower alkyl group, a halo-lower alkyl group, a lower alkoxy group, or a mono- or di-lower alkylamino group.

In the present compound, the substitution pattern of the —NR— group and the methylene group on Ring A is preferably ortho (1,2-substitution) or metha (1,3-substitution).

Further, the preferable compound is the compound of the formula I wherein the methylene group is linked at 3-position to the —NR— group on Ring A; Ring A is a benzene ring which may optionally be substituted by a substituent selected from the group consisting of a lower alkyl group, a halo-lower alkyl group, a halogen atom, a lower alkoxy group, and a phenyl group; and Ring B is an unsaturated 5-or 6-membered monocyclic heterocyclic ring which may optionally be substituted by 1-3 substituents selected from the group consisting of a lower alkyl group, a halo-lower alkyl group, a phenyl-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a mono- or di-lower alkylaminophenyl group, a heterocyclyl group, a haloheterocyclyl group, a lower alkylheterocyclyl group, a lower alkoxyheterocyclyl group, and a mono- or di-lower alkylaminoheterocyclyl group.

Another preferable compound is the compound of the formula I wherein the methylene group is linked at 3-position to the —NR— group on Ring A; Ring A is an unsaturated 5- or 6-membered monocyclic heterocyclic ring which may optionally be substituted by a substituent selected from the group consisting of a lower alkyl group, a halogen atom, a lower alkoxy group, and an oxo group; and Ring B is a benzene ring which is substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a heterocyclyl group, a haloheterocyclyl group, and a lower alkylheterocyclyl group.

A further another preferable compound is the compound of the formula I wherein the methylene group is linked at 3-position to the —NR— group on Ring A; Ring A is an unsaturated 5- or 6-membered monocyclic heterocyclic ring which may optionally be substituted by a substituent selected from the group consisting of a lower alkyl group, a halogen atom, a lower alkoxy group, and an oxo group; and Ring B is an unsaturated 5- or 6-membered monocyclic heterocyclic ring which may optionally be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a heterocyclyl group, a haloheterocyclyl group, and a lower alkylheterocyclyl group.

A further more preferable compound is the compound of the formula I wherein the methylene group is linked at 3-position to the —NR— group on Ring A; Ring A is a benzene ring which may optionally be substituted by a substituent selected from the group consisting of a lower alkyl group, a hydroxy-lower alkyl group, a halo-lower alkyl group, a lower alkoxy-lower alkyl group, a halogen atom, a lower alkoxy group, a halo-lower alkoxy group, a lower alkoxy-lower alkoxy group, and a phenyl group; and Ring B is a benzene ring which may optionally be substituted by 1-3 substituents selected from the group consisting of a lower alkyl group, a halo-lower alkyl group, a phenyl-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a methylenedioxyphenyl group, an ethyleneoxyphenyl group, a mono- or di-lower alkylaminophenyl group, a heterocyclyl group, a haloheterocyclyl group, and a lower alkylheterocyclyl group.

In these preferable compounds, the unsaturated monocyclic heterocyclic ring is preferably furan, thiophene, oxazole, isoxazole, triazole, tetrazole, pyrazole, pyridine, pyrimidine, pyrazine, dihydroisoxazole, dihydropyridine, or thiazole, and the unsaturated fused heterobicyclic ring is preferably indoline, isoindoline, benzothiazole, benzoxazole, indole, indazole, quinoline, isoquinoline, benzothiophene, benzofuran, thienothiophene, or dihydroisoquinoline.

Preferable embodiment of the present invention is the compound of the following formula IA:

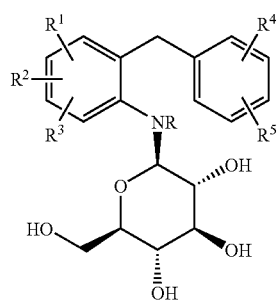

(IA)

wherein $R^1$, $R^2$, and $R^3$, are independently a hydrogen atom, a halogen atom, a hydroxyl group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, a phenyl group, a phenylalkoxy group, a cyano group, a nitro group, an amino group, a mono- or di-alkylamino group, an alkanoylamino group, a carboxyl group, an alkoxycarbonyl group, a carbamoyl group, a mono- or di-alkylcarbamoyl group, an alkanoyl group, an alkylsulfonylamino group, a phenylsulfonylamino group, an alkylsulfinyl group, an alkylsulfonyl group or a phenylsulfonyl group;

$R^4$ and $R^5$ are independently a hydrogen atom; a halogen atom; a hydroxyl group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, alkylenedioxy group, an alkyleneoxy group, or a mono- or di-alkylamino group; or a heterocyclyl group optionally substituted by a halogen atom, a cyano group, an alkyl group, a haloalkyl group, an alkoxy group, or a haloalkoxy group, or $R^4$ and $R^5$ are combined with each other at the terminals thereof to form an alkylene group, and other symbols are as defined above.

Among the compounds of the above formula IA, preferable compounds are the compound of the formula IA wherein $R^1$, $R^2$ and $R^3$ are independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group; $R^4$ and $R^5$ are independently a hydrogen atom; a halogen atom; a lower alkyl group; a halo-lower alkyl group; a phenyl-lower alkyl group; a phenyl group optionally substituted by a halogen atom, a cyano group, a lower alkyl group, a halo-lower alkyl group, a lower alkoxy group, a methylenedioxy group, an ethyleneoxy group, or a mono- or di-lower alkylamino group; or a heterocyclyl group optionally substituted by a halogen atom, or a lower alkyl group, or $R^4$ and $R^5$ are combined with each other at the terminals thereof to form an alkylene group.

Among them, preferred is a compound wherein $R^1$ is a halogen atom, a lower alkyl group, or a lower alkoxy group, $R^2$ and $R^3$ are a hydrogen atom, $R^4$ is a halogen atom; a lower alkyl group; a lower alkoxy group; a phenyl group optionally substituted by a substituent selected from the group consisting of a halogen atom, a cyano group, a lower alkyl group, a halo-lower alkyl group, a lower alkoxy group, and a mono- or di-lower alkylamino group; or a heterocyclyl group optionally substituted by a halogen atom or a lower alkyl group, and $R^5$ is a hydrogen atom.

Especially preferred is a compound wherein the heterocyclyl group is a thienyl group, a pyridyl group, a pyrimidyl group, a pyrazinyl group, a pyrazolyl group, a thiazolyl group, or a quinolyl group.

The compound (I) of the present invention exhibits an excellent inhibitory activity against sodium-dependent glucose transporter, and an excellent blood glucose lowering effect. Therefore, the compound of the present invention is useful in the treatment or the prophylaxis of diabetes mellitus (type 1 and type 2 diabetes mellitus, etc.) or diabetic complications (such as diabetic retinopathy, diabetic neuropathy, diabetic nephropathy, or is useful in the treatment of postprandial hyperglycemia.

The compound (I) of the present invention or a pharmaceutically acceptable salt thereof may be administered either orally or parenterally, and can be used in the form of a suitable pharmaceutical preparation. Suitable pharmaceutical preparation for oral administration includes, for example, solid preparation such as tablets, granules, capsules, powders, etc., or solution preparations, suspension preparations, or emulsion preparations, etc. Suitable pharmaceutical preparation for parenteral administration includes, for example, suppositories; injection preparations and intravenous drip preparations using distilled water for injection, physiological saline solution or aqueous glucose solution; or inhalant preparations.

The dosage of the present compound (I) or a pharmaceutically acceptable salt thereof may vary according to the administration routes, ages, body weight, conditions of a patient, or kinds and severity of a disease to be treated, and it is usually in the range of about 0.1 to 50 mg/kg/day, preferably in the range of about 0.1 to 30 mg/kg/day.

The compound of the formula I may be used, if necessary, in combination with one or more of other antidiabetic agents, and/or one or more agents for treatment of other diseases. The present compound and these other agents may be administered in the same dosage form, in a separate oral dosage form or by injection.

The other antidiabetic agents include, for example, antidiabetic or antihyperglycemic agents including insulin, insulin secretagogues, or insulin sensitizers, or other antidiabetic agents having an action mechanism different from SGLT inhibition, and 1, 2, 3 or 4 of these other antidiabetic agents may preferably be used. Concrete examples thereof are biguanide compounds, sulfonylurea compounds, α-glucosidase inhibitors, PPARγ agonists (e.g., thiazolidinedione compounds), PPARα/γ dual agonists, dipeptidylpeptidase IV (DPP4) inhibitors, mitiglinide compounds, and/or nateglinide compounds, and insulin, glucagon-like peptide-1 (GLP-1), PTP1B inhibitors, glycogen phosphorylase inhibitors and/or glucose 6-phosphatase inhibitors.

The agents for treatment of other diseases include, for example, an anti-obesity agent, an antihypertensive agent, an antiplatelet agent, an anti-atherosclerotic agent and/or a hypolipidemic agent.

The SGLT inhibitors of the formula I may be used in combination with agents for treatment of diabetic complications, if necessary. These agents include, for example, PKC inhibitors and/or ACE inhibitors.

The dosage of those agents may vary according to ages, body weight, and conditions of patients, and administration routes, dosage forms, etc.

These pharmaceutical compositions may be orally administered to mammalian species including human beings, apes, dogs, etc., for example, in the dosage form of tablet, capsule, granule or powder, or parenterally administered in the form of injection preparation, or intranasally, or in the form of transdermal patch.

The present compound of the formula (I) wherein R is a hydrogen atom or a lower alkyl group may be prepared by the following Reaction Scheme 1 or 2.

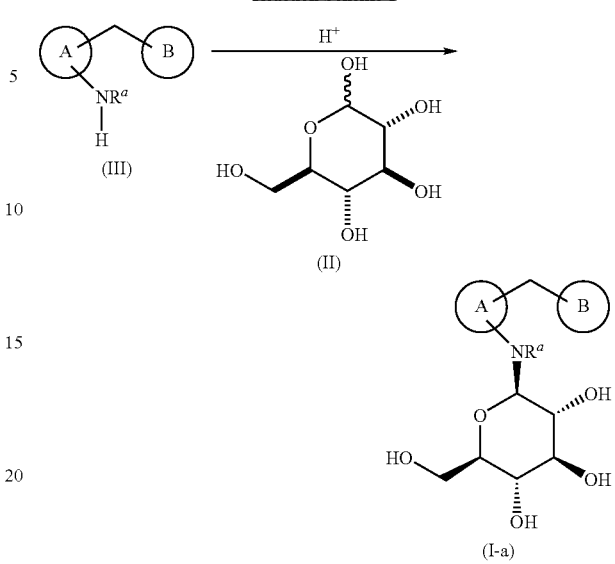

wherein $R^a$ is a hydrogen atom or a lower alkyl group, and the other symbols are as defined above.

First, among the compounds of the formula (I), the compounds of the formula I wherein R is a hydrogen atom or a lower alkyl group may be prepared by condensing the compound of the formula III and the compound of the formula II. The condensation reaction can be carried out in a suitable solvent and if necessary in the presence of an acid.

The acid includes conventional acids used in ordinary acetal exchange reaction, for example, ammonium chloride, ammonium sulfate, hydrochloric acid, etc.

The solvent may be any inert solvent which does not disturb the reaction, for example, ethers such as diethyl ether, diisopropyl ether, tetrahydrofuran, dioxane, 1,2-dimethoxyethane, etc., alcohols such as methanol, ethanol, etc., water, and if desired, a mixture of two or more of these solvents.

This reaction is preferably carried with heating, for example, at a temperature from 50° C. to a boiling point of the solvent used, especially preferably at a temperature of from 50 to 100° C.

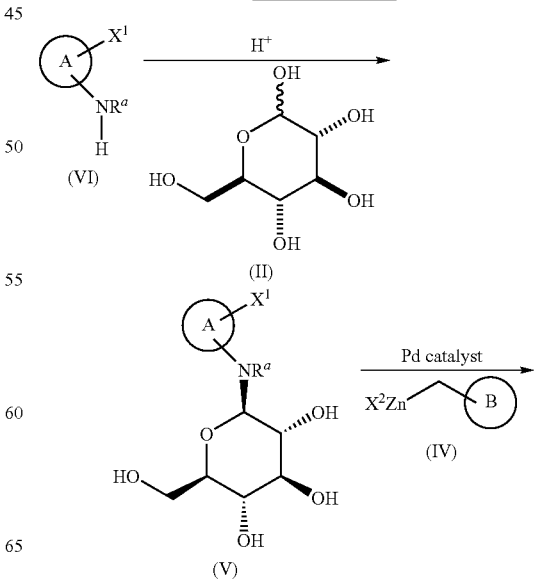

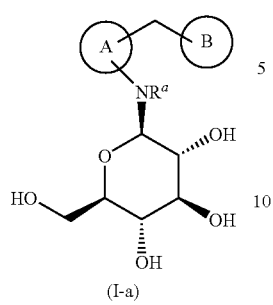

(I-a)

wherein $X^1$ and $X^2$ are independently a halogen atom, and the other symbols are as defined above.

First, the compound of the formula V is prepared by condensing the compound of the formula VI and the compound of the formula II. The condensation reaction can be carried out in a similar manner to the reaction in Reaction Scheme 1.

Then, the compound of the formula I may be prepared by coupling of the compound of the formula V with the compound of the formula IV in the presence of a palladium catalyst, and in the presence or absence of a phosphine ligand in a suitable solvent.

The palladium catalyst may be conventional palladium catalysts such as tetrakis(triphenyl)phosphinepalladium(0), palladium(II) acetate, palladium(II) chloride, bis(triphenyl) phosphinepalladium(II) dichloride, tris(dibenzylideneacetone)dipalladium(0), palladium(II) chloride.1,1'-bis(diphenylphosphino) ferrocene complex, etc.

The phosphine ligand includes, for example, phosphorous compounds such as triphenylphosphine, 1,2-bis(diphenylphosphino)ethane, tri(2-furyl)phosphine, etc.

The solvent may be any inert solvent which does not disturb the reaction, for example, ethers such as diethyl ether, diisopropyl ether, tetrahydrofuran, dioxane, 1,2-dimethoxyethane, etc., amide solvents such as N,N-dimethylformamide, N,N-dimethylacetamide, 1,3-dimethyl-2-imidazolidinone, etc., aromatic hydrocarbons such as benzene, toluene, xylene, etc., dimethylsulfoxide, water, and if desired, a mixture of two or more of these solvents.

This reaction can be carried out at room temperature or with heating, for example, at a temperature of room temperature to a boiling point of the reaction mixture, and especially preferably at a temperature of room temperature to 50° C.

In addition, among the compounds of the formula (I) of the present invention, the compound of the formula (I) wherein R is a lower alkanoyl group or a lower alkoxycarbonyl group may be prepared by a method disclosed in the following Reaction Scheme 3 or 4.

Reaction Scheme 3

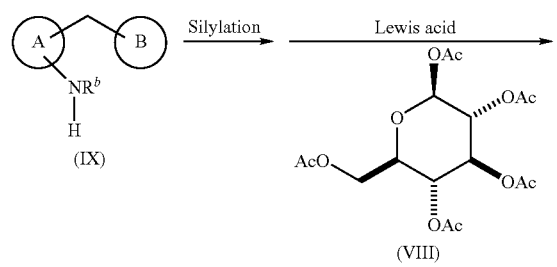

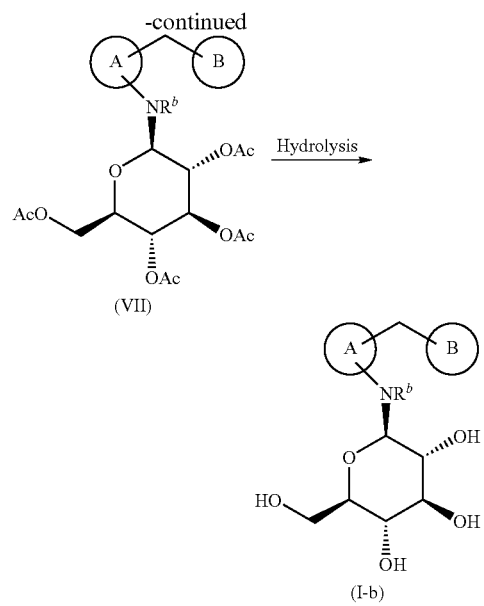

wherein $R^b$ is a lower alkanoyl group or a lower alkoxycarbonyl group, Ac is an acetyl group, and the other symbols are as defined above.

First, the compound of the formula IX is silylated in a solvent. Then, the product is further reacted with an α- or β-D-glucosepentaacetate (i.e., the compound of the formula VIII) to give the compound of the formula VII. Further, the compound of the formula VII is subjected to hydrolysis to give the compound of the formula I-b.

The silylation reaction can be carried out by treating the compound with a silylating agent in a solvent. The silylating agent includes, for example, N,O-bis (trimethylsilyl)acetamide, 1,1,1,3,3,3-hexamethyldisilazane, etc.

The solvent may be any inert solvent which does not disturb the reaction, for example, halogenated hydrocarbons such as dichloromethane, dichloroethane, chloroform, etc., ethers such as diethyl ether, diisopropyl ether, tetrahydrofuran, dioxane, 1,2-dimethoxyethane, etc., acetonitrile, dimethylsulfoxide, etc., and if desired, a mixture of two or more of these solvents.

This reaction is preferably carried out under cooling or with heating, for example, at a temperature of 0° C. to 60° C., preferably at a temperature of room temperature to 60° C.

The reaction with α- or β-D-glucose pentaacetate (i.e., the compound of the formula VIII) can be carried out in a solvent in the presence of a Lewis acid.

The Lewis acid includes, for example, trimethylsilyl trifluoromethanesulfonate, titanium(IV) chloride, tin tetrachloride, boron trifluoride diethyl ether complex.

The solvent may be any inert solvent which does not disturb the reaction, for example, halogenated hydrocarbons such as dichloromethane, dichloroethane, chloroform, etc., ethers such as diethyl ether, diisopropyl ether, tetrahydrofuran, dioxane, 1,2-dimethoxyethane, etc., acetonitrile, dimethylsulfoxide, etc., and if desired, a mixture of two or more of these solvents.

This reaction can be carried out under cooling or with heating, for example, at a temperature of 0° C. to 100° C., more preferably at a temperature of room temperature to 60° C.

The hydrolysis of the compound of the formula VII can be carried out by treating it with a base in a solvent.

The base includes a conventional base used in the hydrolysis, for example, an alkali metal hydroxide such as sodium hydroxide, potassium hydroxide, lithium hydroxide, etc., an alkali metal lower alkoxide such as sodium methoxide, sodium ethoxide, etc.

The solvent may be any inert solvent which does not disturb the reaction, for example, halogenated hydrocarbons such as dichloromethane, dichloroethane, chloroform, etc., ethers such as diethyl ether, diisopropyl ether, tetrahydrofuran, dioxane, 1,2-dimethoxyethane, etc., amide solvents such as N,N-dimethyl formamide, N,N-dimethylacetamide, 1,3-dimethyl-2-imidazolidinone, etc., lower alcohols such as methanol, ethanol, etc., acetonitrile, dimethylsulfoxide, water, and if desired, a mixture of two or more of these solvents.

This reaction is preferably carried out under cooling or with heating, for example, at a temperature of 0° C. to 50° C., more preferably at a temperature of 0° C. to room temperature.

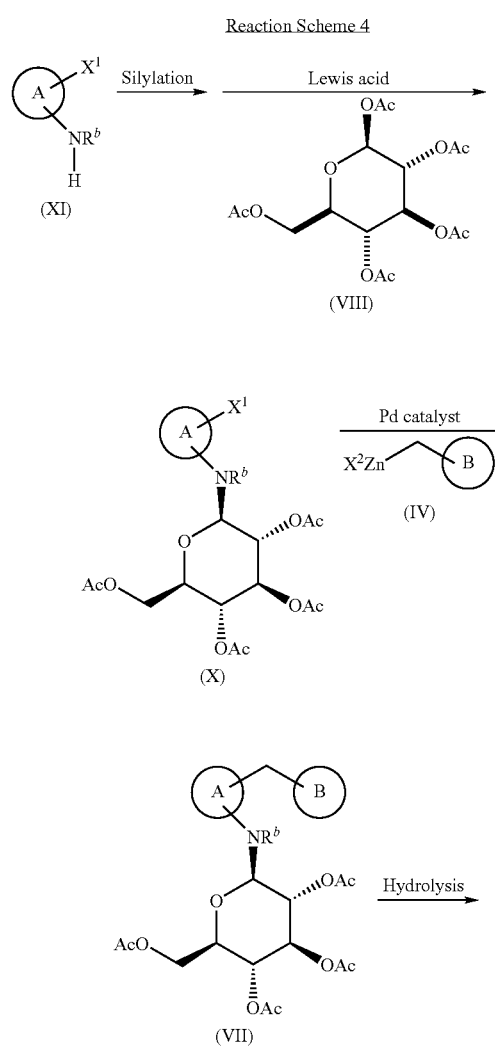

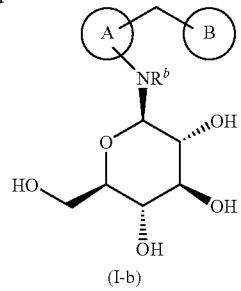

wherein the symbols are as defined above.

First, the compound of the formula XI is silylated in a solvent, and the product thus obtained is reacted with α- or β-D-glucose pentaacetate in the presence of a Lewis acid to give the compound of the formula X. Further, the compound of the formula X is coupled with the compound of the formula IV in the presence of a palladium catalyst, and in the presence or absence of a phosphine ligand, in a suitable solvent to give the compound of the formula VII, which is subjected to hydrolysis to give the compound of the formula I-b.

The silylation reaction of the compound of the formula XI, and the reaction of the silylated compound with α- or β-D-glucose pentaacetate may be carried out in a similar manner to the reaction in Reaction Scheme 3.

The coupling reaction of the compound of the formula X and the compound of the formula IV can be carried out in a similar manner to the reaction in Reaction Scheme 2.

The step of hydrolysis of the compound of the formula VII to give the compound of the formula I-b can be carried out in a similar manner to that in Reaction Scheme 3.

The compound of the present invention thus obtained may be isolated and purified by a conventional method well known in the organic chemistry such as recrystallization, column chromatography, etc.

The compound of the formula III and the compound of the formula IX may be prepared by a method shown in the following Reaction Scheme 5, 6 or 7.

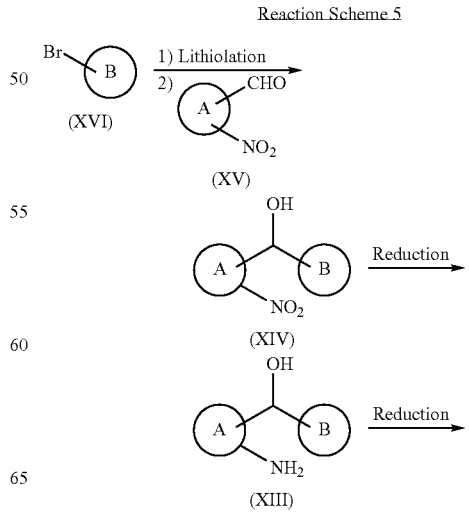

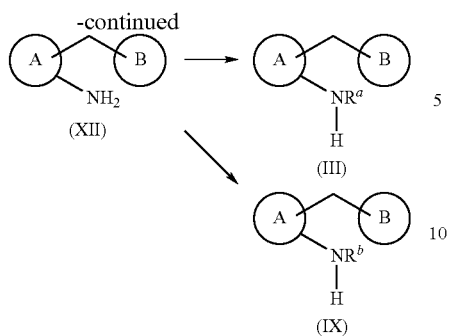

wherein the symbols are as defined above.

The compound of the formula XVI is lithiated, and the product is coupled with the compound of the formula XV in a suitable solvent to give the compound of the formula XIV. For example, the compound of the formula XVI is treated with n-butyl lithium or t-butyl lithium in a suitable solvent such as tetrahydrofuran, diethyl ether, etc. at ~78° C., and further reacted with the compound of the formula XV.

Then, the compound of the formula XIV is subjected to reduction to give the compound of the formula XIII. The reduction can be carried out by catalytic reduction using a palladium catalyst (e.g., palladium-carbon, palladium hydroxide, etc.) in a suitable solvent (e.g., methanol, ethanol, ethyl acetate, etc.) under hydrogen atmosphere.

Further, the compound of the formula XIII is subjected to reduction to give the compound of the formula XII (i.e., the compound of the formula III wherein R is a hydrogen atom). The reduction can be carried out by treating it with a silane reagent (e.g., triethylsilane, triisopropylsilane, etc.) in a suitable solvent (e.g., acetonitrile, dichloromethane, or a mixture of acetonitrile/dichloromethane) in the presence of a Lewis acid (e.g., boron trifluoride.diethylether complex, titanium (IV) tetrachloride, etc.) or an acid (e.g., trifluoroacetic acid, etc.).

Finally, if necessary, the compound of the formula XII is alkylated to give the compound of the formula III, or the compound of the formula XII is acylated to give the compound of the formula IX.

The alkylation reaction can be carried out using an alkylating agent such as a lower alkyl halide (e.g., iodomethane, bromoehtane) in a suitable solvent (e.g., tetrahydrofuran, dichloromethane, ethyl acetate, dimethylformamide, 1,3-dimethyl-2-imidazolidinone, etc.), in the presence of a base (e.g., triethylamine, pyridine, diisopropylethylamine, potassium carbonate, sodium hydrogen carbonate, etc.)

The acylation reaction can be carried out using an acylating agent such as a lower alkanoyl halide or a lower alkoxycarbonyl halide, or an acid anhydride or an ester of a carboxylic acid corresponding thereto, in a suitable solvent (e.g., tetrahydrofuran, dichloromethane, ethylacetate, etc.), in the presence or absence of a base (e.g., triethylamine, pyridine, diisopropylethylamine, etc.).

Further, the compound of the formula III wherein R is a lower alkyl group can be obtained by reducing the compound of the formula III wherein R is a lower alkanoyl group. The reduction can be carried out by a conventional method using a reducing agent (lithium aluminum hydride, diborane, etc.) in a suitable solvent (e.g., tetrahydrofuran, dioxane, etc.).

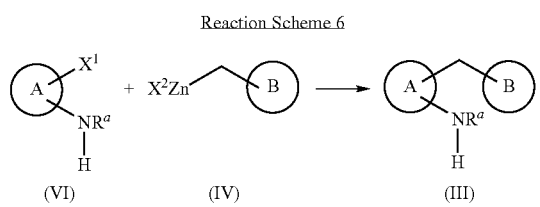

wherein the symbols are as defined above.

The compound of the formula III can be prepared by coupling of the compound of the formula VI with the compound of the formula IV.

The coupling reaction can be carried out in a similar manner to the coupling reaction of the compound of the formula V and the compound of the formula IV in Reaction Scheme 2.

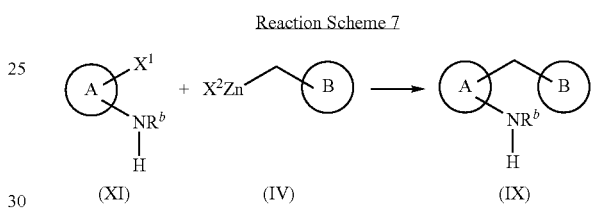

wherein the symbols are as defined above.

The compound of the formula IX may also be prepared by coupling of the compound of the formula XI with the compound of the formula IV.

The coupling reaction can be carried out in a similar manner to the coupling reaction of the compound of the formula V and the compound of the formula IV in Reaction Scheme 2.

The other starting compounds are commercially available or may easily be prepared by a standard method well known to an ordinary skilled person in this field.

Hereinafter, the present invention will be illustrated by Examples, Reference Examples, but the present invention should not be construed to be limited thereto.

EXAMPLE 1

2-(4-Ethylbenzyl)-N-(β-D-glucopyranosyl)aniline

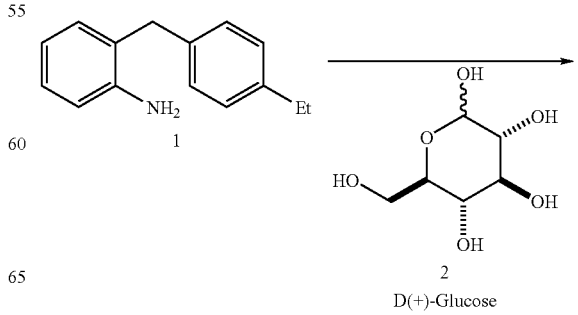

-continued

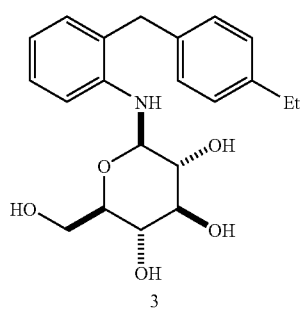

wherein Et is an ethyl group.

2-(4-Ethylbenzyl)aniline 1 (500 mg) was dissolved in methanol (5 ml), and thereto are added D-(+)-glucose 2 (516 mg) and ammonium chloride (25 mg), and the mixture was heated under reflux for 2 hours. Methanol was evaporated under reduced pressure, and water was added to the residue, and the mixture was extracted with ethyl acetate. The extract was washed with brine, dried over sodium sulfate, and the solvent was evaporated. The residue was purified by silica gel column chromatography (chloroform:methanol=40:1-20:1) to give the desired 2-(4-ethylbenzyl)-N-(β-D-glucopyranosyl)aniline 3 (495 mg) as colorless crystals. APCI-Mass m/Z 374 (M+H).

EXAMPLES 2-5

The compounds as shown in Table 1 below were prepared in a similar manner as in Example 1 from the corresponding starting materials.

TABLE 1

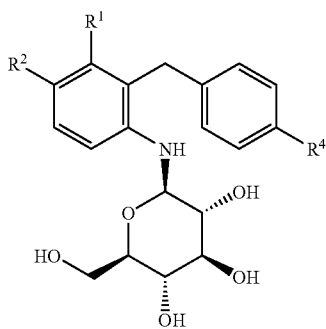

| Examples | $R^1$ | $R^2$ | $R^4$ | APCI-Mass (m/Z) |
|---|---|---|---|---|
| 2 | H | $CF_3$— | —$CH_2CH_3$ | 442 (M + H) |
| 3 | H | H | H | 346 (M + H) |
| 4 | H | F | —$CH_2CH_3$ | 392 (M + H) |
| 5 | F | F | —$CH_2CH_3$ | 410 (M + H) |

REFERENCE EXAMPLE 1

2-(4-Ethylbenzyl)aniline

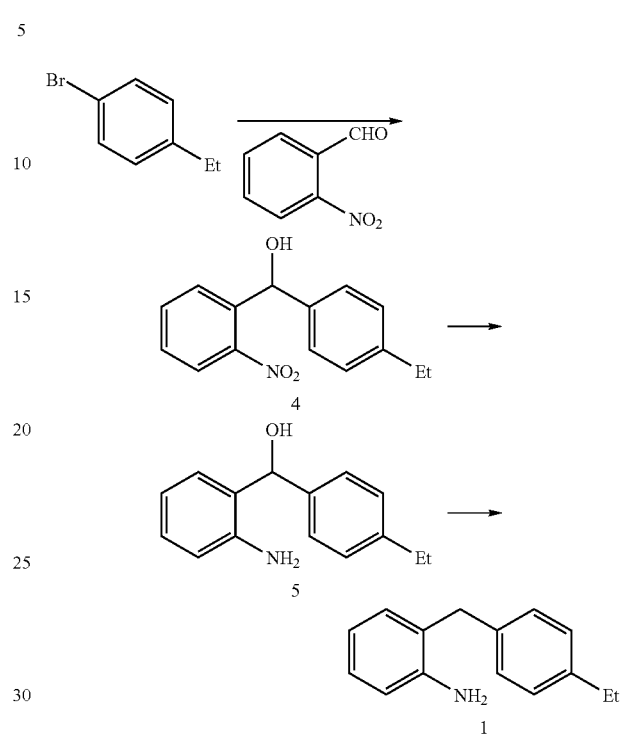

wherein the symbols are as defined above.

(1) A solution of 1-bromo-4-ethylbenzene (6.43 g) in tetrahydrofuran (50 ml) was cooled to ~78° C. under argon atmosphere, and thereto was added dropwise n-butyl lithium (2.6 M hexane solution 14.0 ml). The mixture was stirred at the same temperature for 30 minutes, and the reaction solution was added dropwise to a solution of o-nitrobenzaldehyde (5.0 g) in tetrahydrofuran (50 ml) at ~78° C. The mixture was stirred at the same temperature for 30 minutes, and warmed to 0° C. over a period of one hour. To the mixture was added an aqueous ammonium chloride solution, and the mixture was extracted with ethyl acetate, dried over sodium sulfate, and the solvent was evaporated under reduced pressure. The residue was purified by silica gel column chromatography (hexane:ethyl acetate=10:1) to give the compound 4 (2.26 g) as colorless oil. APCI-Mass m/Z 275 (M+$NH_4$).

(2) The above compound 4 (1.85 g) was dissolved in ethanol (74 ml), and thereto was added wet palladium-carbon (370 mg). The mixture was stirred at room temperature under hydrogen atmosphere for 4 hours. The catalyst was removed by filtration, and the filtrate was evaporated under reduced pressure to give the compound 5 (1.58 g) as colorless solid. APCI-Mass m/Z 210 (M+H—$H_2O$).

(3) The above compound 5 (1.53 g) was dissolved in acetonitrile (45 ml), and the mixture was cooled to −30° C., and thereto was added dropwise boron trifluoride.diethyl ether complex (1.71 ml). Then, triethylsilane (2.15 ml) was added thereto, and the mixture was stirred at the same temperature for one hour. The mixture was warmed to 0° C. over a period of 30 minutes, and the mixture was further stirred at room temperature for 1.5 hour. To the mixture was added a saturated aqueous sodium hydrogen carbonate solution, and the mixture was extracted with ethyl acetate. The extract was washed with brine, dried over sodium sulfate, and the solvent was evaporated under reduced pressure. The residue was purified by silica gel column chromatography (hexane:ethyl acetate=24:1) to give the desired 2-(4-ethylbenzyl)aniline 1 (1.07 g) as colorless oil. APCI-Mass m/Z 212 (M+H).

REFERENCE EXAMPLE 2

2-(4-Ethylbenzyl)-4-trifluoromethylaniline

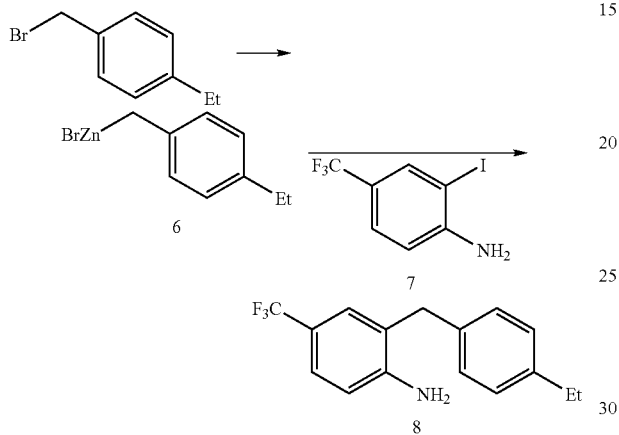

(1) A mixture of zinc powder (817 mg) and 1,2-dibromoethane (0.044 ml) in dimethylformamide (25 ml) was stirred with heating at 70° C. for 10 minutes. The reaction solution was cooled to room temperature, and thereto was added chlorotrimethylsilane (0.050 ml), and further stirred for 30 minutes. To the mixture was added dropwise a solution of 4-ethylbenzyl bromide (1.99 g) in dimethylformamide (10 ml) at 0° C. over a period of 2 hours. The mixture was stirred at the same temperature for 2 hours to give a solution of the compound 6.

(2) The above solution of the compound 6 was mixed with a solution of tris(dibenzylideneacetone)palladium(0) (140 mg), tri(2-furyl)phosphine (120 mg) and 4-amino-3-iodobenzo trifluoride 7 (1.44 g) in tetrahydrofuran (30 ml), and the mixture was stirred overnight at room temperature under argon atmosphere. The reaction solution was poured into water, and the mixture was extracted with ethyl acetate. The extract was washed with brine, dried over sodium sulfate, and the solvent was evaporated under reduced pressure. The residue was purified by silica gel column chromatography (hexane:ethyl acetate=9:1) to give the desired 2-(4-ethylbenzyl)-4-trifluoromethylaniline 8 (866 mg) as colorless oil. APCI-Mass m/Z 280 (M+H).

REFERENCE EXAMPLE 3

2-(4-Ethylbenzyl)-4-fluoroaniline (1) A mixed solution of 4-fluoroaniline (1.00 g), iodine (2.28 g) and silver sulfate (2.81 g) in ethanol (180 ml) was stirred at room temperature for one hour. Insoluble materials were filtered off, and the solvent of the filtrate was evaporated under reduced pressure. The residue was purified by silica gel column chromatography (hexane:ethyl acetate=19:1) to give 4-fluoro-2-iodoaniline (1.16 g) as colorless oil. ESI-Mass m/Z 236 (M−H).

(2) The above 4-fluoro-2-iodoaniline was treated in a similar manner as in Reference Example 2 to give 2-(4-ethylbenzyl)-4-fluoroaniline as powder. APCI-Mass m/Z 230 (M+H).

REFERENCE EXAMPLE 4

3,4-Difluoro-2-(4-ethylbenzyl)aniline 3,4,-Difluoro-2-iodoaniline (see S. Morita et al., *Tetrahedron Asymmetry* (1995) 6 245) was treated in a similar manner as in Reference Example 2 to give the desired 3,4-difluoro-2-(4-ethylbenzyl)aniline as powder. APCI-Mass m/Z 247 (M+H).

The invention claimed is:
1. A compound represented by the following formula IA:

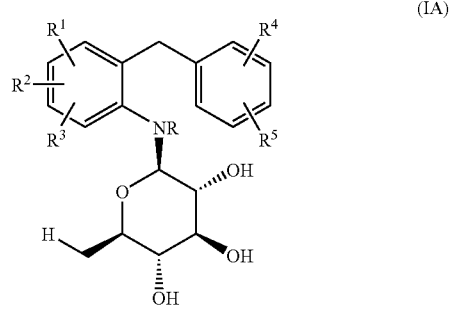

wherein $R^1$, $R^2$, and $R^3$, are independently a hydrogen atom, a halogen atom, a hydroxyl group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a phenyl group, a phenylalkoxy group, a cyano group, a nitro group, an amino group, a mono- or di-alkylamino group, an alkanoylamino group, a carboxyl group, an alkoxycarbonyl group, a carbamoyl group, a mono- or di-alkylcarbamoyl group, an alkanoyl group, an alkylsulfonylamino group, a phenylsulfonylamino group, an alkylsulfinyl group, an alkylsulfonyl group or a phenylsulfonyl group;

$R^4$ and $R^5$ are independently a hydrogen atom; a halogen atom; a hydroxyl group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, an alkylenedioxy group, an alkyleneoxy group, or a mono- or di-alkylamino group; or a heterocyclyl group optionally substituted by a halogen atom, a cyano group, an alkyl group, a haloalkyl group, an alkoxy group, or a haloalkoxy group, or $R^4$ and $R^5$ are combined with each other at the terminals thereof to form an alkylene group; and R is a hydrogen atom, a lower alkyl group, a lower alkanoyl group or a lower alkoxycarbonyl group, or a pharmaceutically acceptable salt thereof.

2. The compound, or the pharmaceutically acceptable salt thereof according to claim 1, wherein $R^1$, $R^2$ and $R^3$ are independently a hydrogen atom, a halogen atom, a lower alkyl group, a hydroxy-lower alkyl group, a halo-lower alkyl group, a lower alkoxy-lower alkyl group, a lower alkoxy group, a halo-lower alkoxy group, or a lower alkoxy-lower alkoxy group;

$R^4$ and $R^5$ are independently a hydrogen atom; a halogen atom; a lower alkyl group; a halo-lower alkyl group; a phenyl-lower alkyl group; a phenyl group optionally substituted by a halogen atom, a cyano group, a lower alkyl group, a halo-lower alkyl group, a lower alkoxy group, a methylenedioxy group, an ethyleneoxy group, or a mono- or di-lower alkylamino group; or a heterocyclyl group optionally substituted by a halogen atom, or a lower alkyl group, or $R^4$ and $R^5$ are combined with each other at the terminals thereof to form an alkylene group.

3. The compound, or the pharmaceutically acceptable salt thereof according to claim 1, wherein $R^1$ is a halogen atom, a lower alkyl group, or a lower alkoxy group, $R^2$ and $R^3$ are a hydrogen atom, $R^4$ is a halogen atom; a lower alkyl group; a lower alkoxy group; a phenyl group optionally substituted by a substituent selected from the group consisting of a halogen atom, a cyano group, a lower alkyl group, a halo-lower alkyl group, a lower alkoxy group, and a mono- or di-lower alkylamino group; or a heterocyclyl group optionally substituted by a halogen atom or a lower alkyl group, and $R^5$ is a hydrogen atom.

4. The compound, or the pharmaceutically acceptable salt thereof according to claim 1, wherein the heterocyclyl group is a thienyl group, a pyridyl group, a pyrimidyl group, a pyrazinyl group, a pyrazolyl group, a thiazolyl group, a quinolyl group, or a tetrazolyl group.

5. A pharmaceutical composition which comprises the compound, or the pharmaceutically acceptable salt thereof as set forth in claim 1, and a pharmaceutically acceptable carrier.

6. A method for treating or delaying the progression or onset of diabetes, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis or hypertension, which comprises administering to a mammalian species in need of treatment a therapeutically effective amount of the compound, or the pharmaceutically acceptable salt thereof as set forth in claim 1.

7. A process for preparing a compound of formula IA:

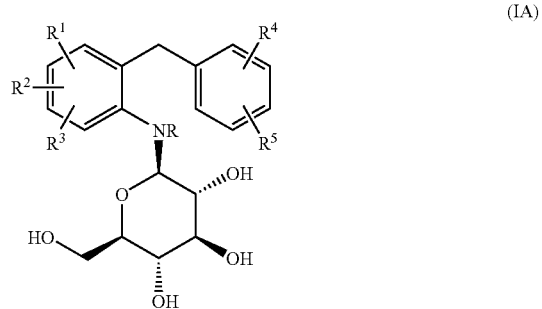

(IA)

wherein the symbols are the same as defined in claim 1, which comprises condensing a compound of formula:

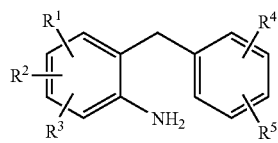

wherein the symbols are the same as defined above, and a compound of formula II:

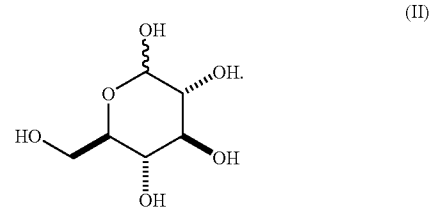

(II)

* * * * *